United States Patent
Yamaguchi et al.

(10) Patent No.: US 9,335,308 B2
(45) Date of Patent: May 10, 2016

(54) CHROMATOGRAPHY SYSTEM, SIGNAL PROCESSING APPARATUS, CHROMATOGRAPHY DATA PROCESSING APPARATUS, AND PROGRAM

(71) Applicant: JASCO Corporation, Tokyo (JP)

(72) Inventors: Takayuki Yamaguchi, Tokyo (JP); Tomonari Watabe, Tokyo (JP)

(73) Assignee: JASCO Corporation, Tokyo (JP)

( * ) Notice: Subject to any disclaimer, the term of this patent is extended or adjusted under 35 U.S.C. 154(b) by 0 days.

(21) Appl. No.: 14/206,801

(22) Filed: Mar. 12, 2014

(65) Prior Publication Data

US 2014/0268154 A1    Sep. 18, 2014

(30) Foreign Application Priority Data

Mar. 12, 2013  (JP) ................................. 2013-049203

(51) Int. Cl.
| | |
|---|---|
| *G01N 30/74* | (2006.01) |
| *G01J 1/04* | (2006.01) |
| *G01N 30/86* | (2006.01) |
| *G01N 21/05* | (2006.01) |

(52) U.S. Cl.
CPC ............... *G01N 30/74* (2013.01); *G01J 1/0488* (2013.01); *G01N 30/8624* (2013.01); *G01N 30/8641* (2013.01); *G01N 21/05* (2013.01)

(58) Field of Classification Search
CPC .......... G01N 30/8641; G01N 30/8624; G01N 21/05; G01J 30/8641; G01J 30/8624; G01J 1/0488
See application file for complete search history.

(56) References Cited

U.S. PATENT DOCUMENTS

| | | | | |
|---|---|---|---|---|
| 5,141,609 | A | * | 8/1992 | Sweedler ......... G01N 27/44721 204/452 |
| 5,813,403 | A | * | 9/1998 | Soller .................. A61B 5/0075 600/310 |

(Continued)

FOREIGN PATENT DOCUMENTS

| | | |
|---|---|---|
| JP | H08-3483 B2 | 1/1996 |
| JP | H10-104215 A | 4/1998 |

(Continued)

OTHER PUBLICATIONS

Office Action in counterpart Japanese Patent Application No. 2013-049203, mailed Jul. 17, 2013 (11 pages).

*Primary Examiner* — Michael A Lyons
*Assistant Examiner* — Dominic J Bologna
(74) *Attorney, Agent, or Firm* — Osha Liang LLP

(57) ABSTRACT

A chromatography system has a multi-channel detection device including a flow cell, optics for directing light from light sources to the flow cell and outputting light that has passed through the flow cell, and a multi-channel detector. The optics has a function of dispersing light in wavelength in an optical path. The detector receives the light dispersed in wavelength. The multi-channel detection device also has a signal processing part connected to the detector. The chromatography system has a data processing apparatus. The signal processing circuit has a function of calculating an absorbance by absorbance=$-\log_{10}(I/I_0)$ using the intensity I of light having a wavelength to be measured that is outputted from the detector and a reference intensity $I_0$ of light that is an average of intensities of light having different wavelengths that is produced at the same point of time as the light having a wavelength to be measured.

6 Claims, 7 Drawing Sheets

(56) References Cited

U.S. PATENT DOCUMENTS

| | | | |
|---|---|---|---|
| 6,111,255 A * | 8/2000 | Malins | 250/339.12 |
| 2001/0000150 A1 * | 4/2001 | Malins | 435/6 |
| 2004/0068163 A1 * | 4/2004 | Ruchti et al. | 600/316 |
| 2008/0106735 A1 * | 5/2008 | Becker-Ross et al. | 356/328 |

FOREIGN PATENT DOCUMENTS

| | | |
|---|---|---|
| JP | 2004-257835 A | 9/2004 |
| JP | 4419637 B2 | 2/2010 |

* cited by examiner (a)

CHROMATOGRAPHY SYSTEM, SIGNAL PROCESSING APPARATUS, CHROMATOGRAPHY DATA PROCESSING APPARATUS, AND PROGRAM

BACKGROUND

1. Field of the Invention

The present invention relates to a chromatography system, a signal processing apparatus, a chromatography data processing apparatus, and a program. More particularly, the present invention relates to technology of reducing variations of a baseline.

2. Description of the Related Art

One of general detectors used for liquid chromatography includes a multi-channel detection device employing a photodiode array or a solid-state imaging device, which is hereinafter referred to as a PDA detector. The PDA detector is configured to perform detection with use of specimen's characteristics of absorbing light having specific wavelengths. For example, the PDA detector may measure the intensity of light incident to a specimen and the intensity of light emitted from the specimen and then calculate an absorbance from a difference between those measured intensities or calculate a concentration of the specimen from such a calculated absorbance.

In a PDA detector, components to be analyzed is flowed and measured through a flow cell. One of analysis methods used for liquid chromatography includes a gradient elution method, which uses a plurality of eluants having different characteristics such as pH or concentration and varies the composition of the eluants in a continuous manner as the analysis progresses. Thus, the type and composition of a liquid within a flow cell is varied as the analysis progresses in a gradient elution method. However, any liquid has an inherent index of refraction. Therefore, the index of the interior of the flow cell is varied. This variation causes light to be emitted from the flow cell to a different degree of refraction, resulting in varied intensities of light that reaches the detector. Since the intensity of light that reaches the detector is thus varied, a phenomenon that the absorbance is seemingly varied is encountered. With analysis using a gradient elution method, this phenomenon causes the shape of the baseline to be changed into a curved line due to the influence of the index of refraction even if an eluant does not absorb light. Furthermore, in a detector for measuring an absorbance, such as a PDA detector, such changes adversely affect the accuracy and precision of qualitative analysis or quantitative analysis.

In order to suppress such variations of a baseline which results from a gradient elution method, for example, a tapered flow cell as shown in FIG. 1(b) has been used instead of a general flow cell (straight type flow cell) in which a passage is cylindrical as shown in FIG. 1(a). Either flow cell has a body 1 made of stainless, for example, an incident window plate 2 made of silica glass, for example, and an emission window plate 3 made of silica glass, for example. A passage 4 extends through the body 1. The incident window plate 2 is disposed on one end of the passage 4 (on the left end of the passage 4 in FIGS. 1(a) and 1(b)). The emission window plate 3 is disposed on the other end of the passage 4 (on the right end of the passage 4 in FIGS. 1(a) and 1(b)). As is apparent from FIGS. 1(a) and 1(b), the passage 4 of the straight type flow cell is in the form of a cylinder having an inside diameter that is uniform over the length of the passage 4 (see FIG. 1(a)), and the passage 4 (see FIG. 1(b)) of the tapered flow cell is in the form of a truncated cone having an inner shape gradually widened along the travelling direction of the light. For example, JP-B H08-3483 discloses such a tapered flow cell.

For example, upon use of a general flow cell (straight type flow cell) in which a passage is cylindrical as shown in FIG. 1(a), if incident light is focused at the vicinity of an inlet of the flow cell, it impinges on a wall downstream of the passage, thereby causing losses. Accordingly, the intensity of light that reaches the detector is lowered.

In contrast, with a tapered flow cell of JP-B H08-3483 as shown in FIG. 1(b), for example, an angle of the incident light coincides with an angle of a wall of an inner circumferential surface of the passage 4 in the flow cell. Thus, the incident light is designed to be unlikely to impinge on the wall of the passage 4. Accordingly, variations in intensity of emitted light that are caused by variations in index of refraction can be suppressed.

Meanwhile, a deuterium lamp, a tungsten lamp, or the like is generally used in a PDA detector. Those lamps have characteristics that the intensity of emitting light varies depending upon variations of environmental temperatures. The variations of environmental temperatures reflect the measurement results as a drift of the baseline. The lamp is a heat source as well as a light source. If the lamp continuously emits light, the surrounding environmental temperature increases due to heat produced by the lamp. Particularly, with liquid chromatography, measurement is performed continuously for several minutes to several tens of minutes. Therefore, variations of the environmental temperatures greatly affect the drift of the baseline. In order to solve such a problem, there has been proposed to provide an air-cooling mechanism in a light source room that accommodates a light source as disclosed in JP-B 4419637. This cooling mechanism controls the temperature of the light source room to be constant.

As described above, various methods have heretofore been proposed to improve the drift of the baseline. However, those methods do not demonstrate satisfactory effects. For example, with the tapered flow cell disclosed in JP-B H08-3483, light incident on the flow cell is refracted at an interface between air and quartz and an interface between quartz and an eluant (liquid) because the indexes of refraction differ between air and quartz and between quartz and the eluant. In a gradient elution method, the type of the eluant is changed as the analysis progresses. As a result, the index of refraction between the cell window plate and the eluant changes. Accordingly, light that would not come out because of impingement on a wall of the flow cell (see FIG. 1(a)) is allowed to come out. Thus, the intensity of light that reaches a detector increases.

As described above, in a tapered flow cell, an angle of incident light coincides with an angle of a wall of the flow cell such that incident light is unlikely to impinge on the wall. However, the incident light cannot completely be controlled when the index of refraction varies to a large degree as shown in FIG. 1(c).

The method of stabilizing the operating temperature of a lamp as disclosed in JP-B 4419637 may require an increased number of parts, resulting in an increased cost of production. Furthermore, with such a method, a function of adjusting the temperature may not properly work when the room temperature changes due to air-conditioning or the like.

SUMMARY

In order to solve the above problems, (1) a chromatography system according to the present invention has a flow cell to which a specimen is supplied, optics for directing light to the flow cell and outputting light that has passed through the flow cell, and a detector disposed on an output of the optics. The optics has a function of dispersing light in wavelength. The detector receives the light dispersed in wavelength. The chromatography system also has a signal processing part connected to the detector. The signal processing part obtains a chromatogram from an intensity of light having a wavelength to be measured that has been outputted from the multi-channel detection device. The signal processing part has a correction function of performing a correction process of a baseline based upon an intensity of light having a wavelength different than the wavelength to be measured at the same point of time upon obtaining the chromatogram.

(2) A chromatography system has a multi-channel detection device having a flow cell to which a specimen is supplied, optics for directing light to the flow cell and outputting light that has passed through the flow cell, and a detector disposed on an output of the optics. The optics has a function of dispersing light in wavelength. The detector receives the light dispersed in wavelength. The chromatography system also has a data processing apparatus operable to perform data analysis on a chromatogram of time-series data outputted from the multi-channel detection device. The data processing apparatus has a correction function of performing a correction process of a baseline on the chromatogram outputted from the multi-channel detection device based upon an intensity of light having a wavelength different than a wavelength to be measured at the same point of time.

For example, variations of the baseline due to variations in index of refraction with a gradient elution method are found over the measured range of wavelengths. Furthermore, although the amount of variation of the baseline may be different depending upon the wavelength, the same tendency of variations is exhibited on each wavelength. For example, if the baseline at the measured wavelength varies so as to increase in the plus direction, then the baselines at wavelengths other than the measured wavelength vary so as to increase in the plus direction at the same point of time and do not vary in the minus direction. Therefore, according to the invention described in Items (1) and (2), influence of variations of the baseline at the wavelength to be measured is reduced by correcting the baseline with the intensity of light that produces variations of the baseline in the same direction as the intensity of light having a wavelength to be measured and has a wavelength different than the light having a wavelength to be measured at the same point of time. This can reduce influence of variations of the baseline caused by various factors, which include not only variations of the baseline caused by changes in index of refraction with a gradient elution method, but also variations of the baseline caused by changes in operation temperature of a light source, for example.

(3) The wavelength different than the wavelength to be measured at the same point of time that is used by the correction function may include a plurality of different wavelengths. With this configuration, it is possible to reduce influence of noise included in the intensity of light having a wavelength different than the measured wavelength.

(4) The correction function may calculate an absorbance by $$absorbance = -\log_{10}(I/I_0)$$

where $I$ is an intensity of light having a wavelength to be measured, and $I_0$ is a reference intensity of light.

The reference intensity of light may be set based upon the intensity of light having a wavelength different than the wavelength to be measured at the same point of time.

(5) In this case, the reference intensity of light may be an average of intensities of light having a plurality of different wavelengths.

(6) A signal processing apparatus according to the present invention is used in a chromatography system having a flow cell to which a specimen is supplied, optics for directing light to the flow cell and outputting light that has passed through the flow cell, and a detector disposed on an output of the optics. The optics has a function of dispersing light in wavelength. The detector receives the light dispersed in wavelength. The signal processing device is connected to the detector of a multi-channel detection device. The signal processing device obtains a chromatogram from an intensity of light having a wavelength to be measured that has been outputted from the detector. The signal processing device has a correction function of performing a correction process of a baseline based upon an intensity of light having a wavelength different than the wavelength to be measured at the same point of time.

(7) A chromatography data processing apparatus according to the present invention is operable to perform data analysis on a chromatogram with a parameter set for the chromatogram. The chromatography data processing apparatus has a correction function of performing a correction process of a baseline on the chromatogram based upon an intensity of light having a wavelength different than a wavelength to be measured at the same point of time.

(8) A program according to the present invention is for implementing the correction function of the chromatography system as described in any one of Items (1) to (5) with a computer.

According to the present invention, the baseline is corrected with the intensity of light having a wavelength different than a wavelength to be measured that is produced at the same point of time as the light having the wavelength to be measured. Therefore, it is possible to effectively suppress variations and drifts of the baseline that would be caused by various factors.

The above and other objects, features, and advantages of the present invention will be apparent from the following description when taken in conjunction with the accompanying drawings which illustrate preferred embodiments of the present invention by way of example.

DETAILED DESCRIPTION OF THE PREFERRED EMBODIMENTS

A chromatography system to embodiments of the present invention will be described below with reference to FIGS. 2 to 7.

Figure 1:
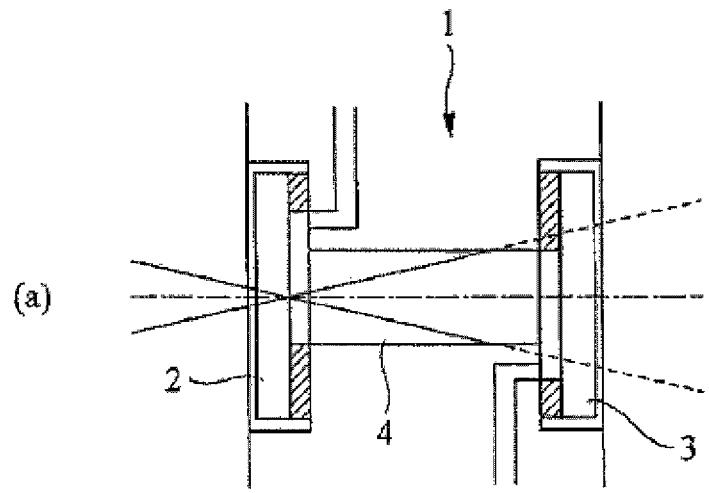
FIGS. 1(a) to 1(c) are diagrams showing structures of flow cells and explaining effects of the index of refraction with different types of flow cells.
Figure 1:
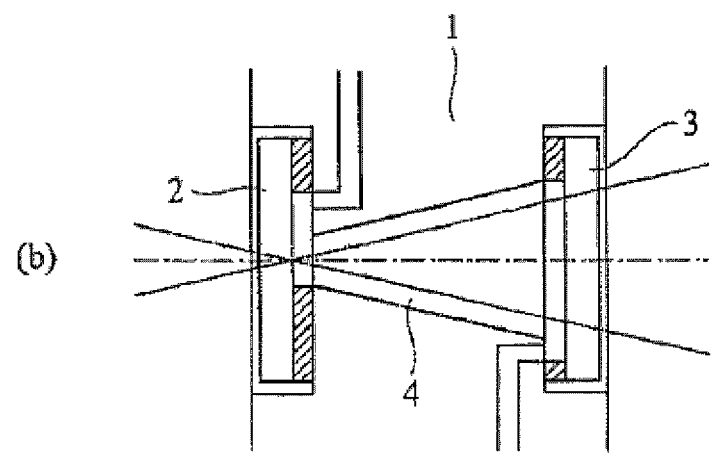
Figure 1:
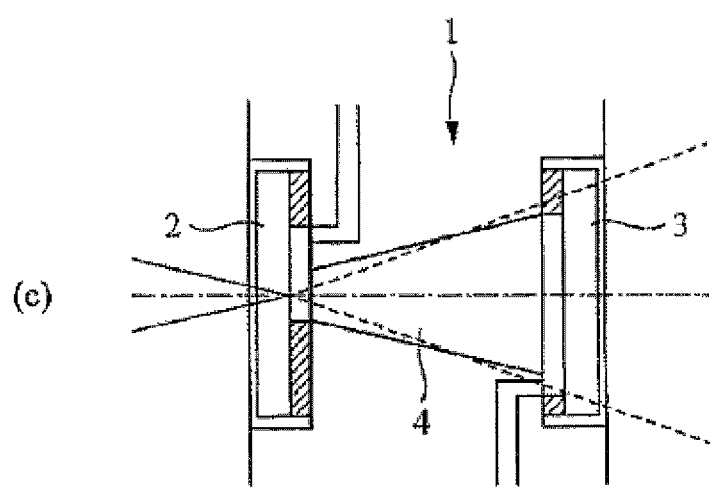
Figure 2:
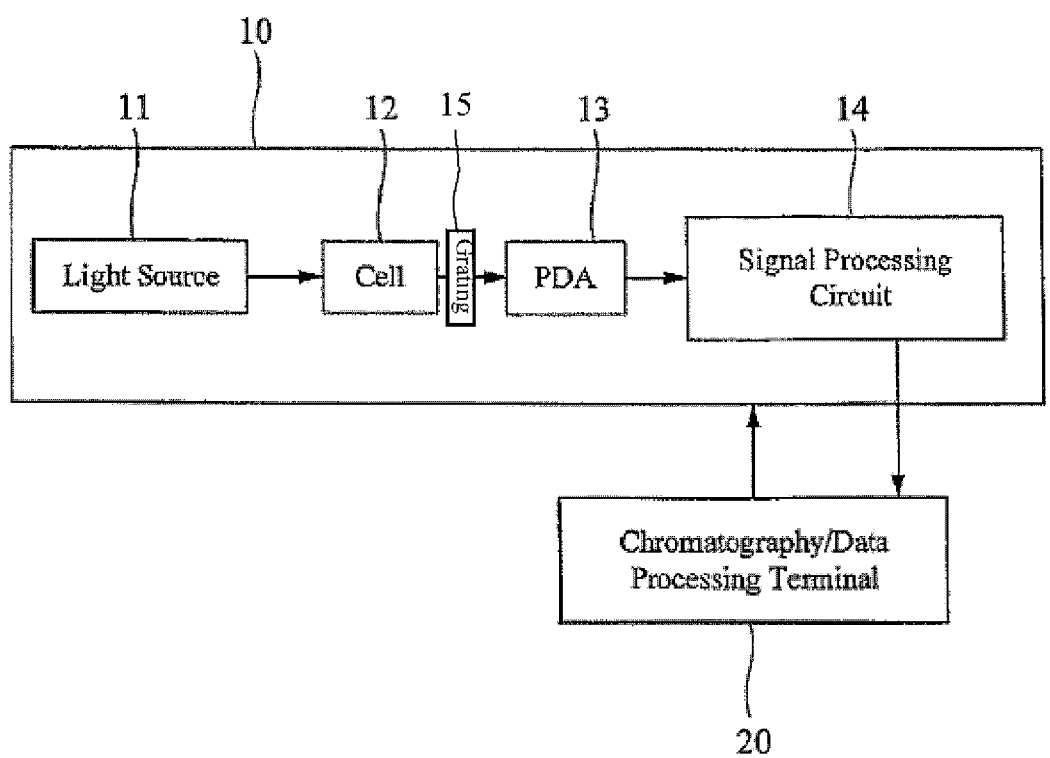
FIG. 2 is a block diagram showing a preferred embodiment of the present invention.
Figure 3:
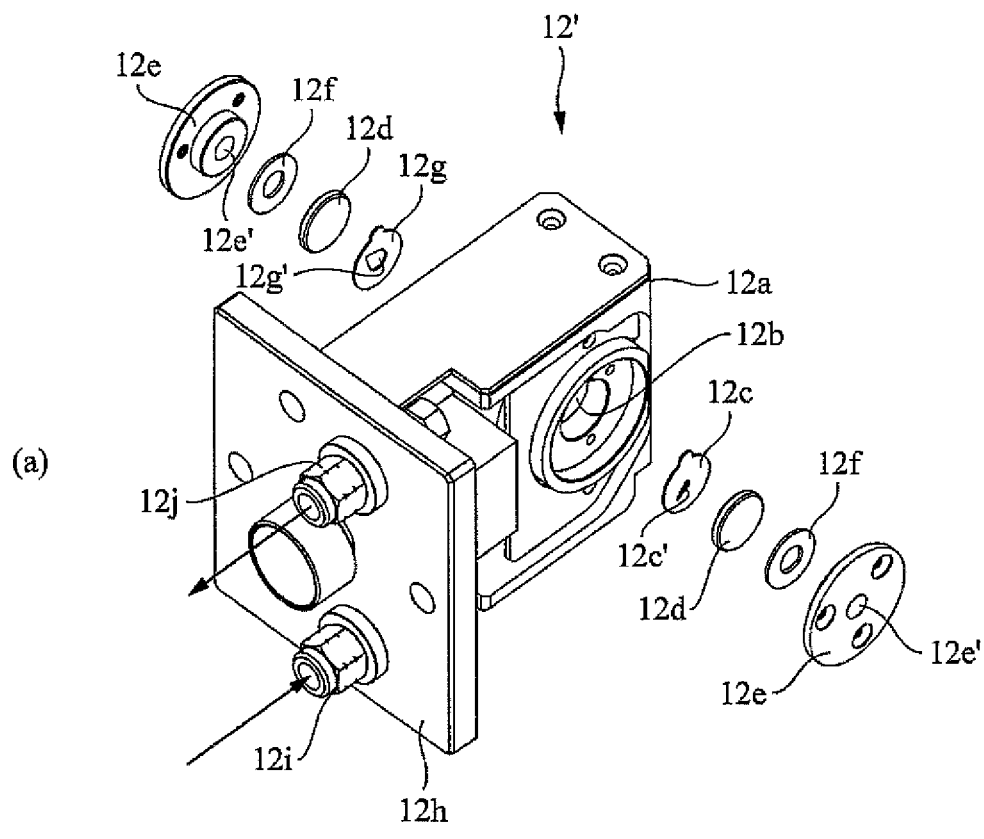
FIGS. 3(a) and 3(b) are diagrams showing an example of a flow cell.
Figure 3:
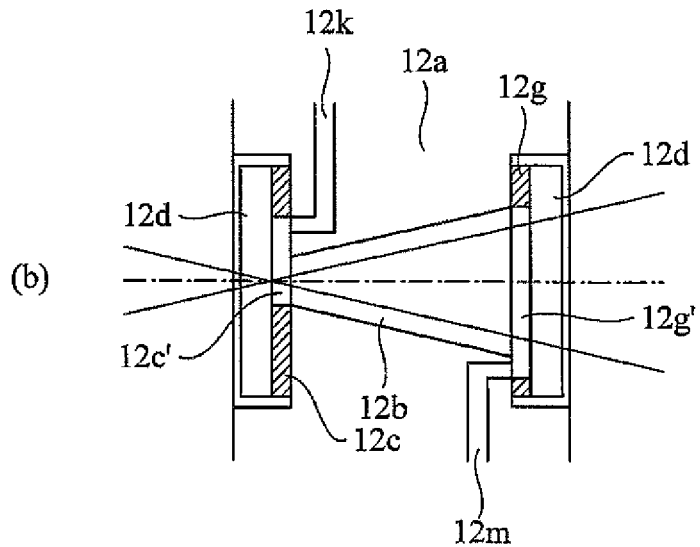

FIG. 2 shows an embodiment of a chromatography system according to the present invention. As shown in FIG. 2, the chromatography system includes a multi-channel detection device 10 operable to perform analysis such as liquid chromatography and supercritical fluid chromatography and a chromatography data processing apparatus 20 operable to acquire data (chromatogram) outputted from the multi-channel detection device 10 and perform data analysis on those data.

The multi-channel detection device 10 has light sources 11, a flow cell 12, a detector 13, and a signal processing circuit 14. The multi-channel detection device 10 also has a mechanism of supplying an unknown specimen or a standard specimen to be analyzed into the flow cell 12 of the detection device through a column and then discharging the specimen. The multi-channel detection device 10 includes optics for directing light from the light sources 11 to the flow cell 12 and for detecting light that has passed through the flow cell 12 (the specimen within the flow cell 12). The detector 13 is disposed in connection with an output of the optics. For example, the detector 13 includes a photodiode array (PDA). The detector 13 may include a solid-state imaging device such as CMOS or CCD. The detector 13 is connected to the signal processing circuit 14.

For example, the optics between the light sources 11 and the flow cell 12 or the optics between the flow cell 12 and the detector 13 include an optical part for dispersing the wavelength of light, such as a diffraction grating 15. Light dispersed in wavelengths is received by the detector 13. The detector 13 outputs electric signals corresponding to the intensities of the lights. Those electric signals are subjected to predetermined signal processing by the signal processing circuit 14 and outputted in time sequence. Those outputted time-series data are used as chromatograms.

For example, the flow cell 12 may employ a flow cell unit 12' having a structure shown in FIGS. 3(a) and 3(b). Specifically, the flow cell unit 12' has a body 12a produced by processing stainless steel or the like. The body 12a includes a passage 12b formed therein so as to extend through the body 12a. A specimen and/or an eluant flows through the passage 12b. The flow cell unit 12' also has a panel 12h arranged on a front side of the body 12a, an inlet pipe connection part 12i provided on the panel 12h, and an outlet pipe connection part 12j provided on the panel 12h. Those pipe connection parts 12i and 12j are connected to stainless pipes for chromatography (not shown). Thus, a specimen and/or an eluant is supplied to and discharged from the body 12a. The pipe connection parts 12i and 12j are respectively communicated with inner passages 12k and 12m formed within the body 12a.

The internal passage 12k, which is located upstream of the flow cell, has an outlet formed on the same surface of the body 12a as an inlet of the passage 12b is formed. The internal passage 12m, which is located right after the flow cell, has an inlet formed on the same surface of the body 12a as an outlet of the passage 12b is formed. The surface on the inlet of the passage 12b is sealed by a gasket 12c, and the surface on the outlet of the passage 12b is sealed by a gasket 12g. The gasket 12c has a hole 12c' formed therein, and the gasket 12g has a hole 12g' formed therein. Thus, the outlet of the internal passage 12k, which is located upstream of the flow cell, the inlet of the passage 12b in the flow cell, the outlet of the passage 12b in the flow cell, and the inlet of the internal passage 12m, which is located right after the flow cell, are connected so as to form a flow path. In the present embodiment, the passage 12b of the flow cell 12 has a tapered shape. Therefore, the inlet hole and the outlet hole of the flow cell 12 have different sizes. Accordingly, the hole 12c' of the gasket 12c and the hole 12g' of the gasket 12g have different sizes and shapes.

Furthermore, the flow cell unit 12' includes cell window plates 12d brought into intimate contact with outer surfaces of the gaskets 12c and 12g. Silica glass or the like is used for the cell window plates 12d. The holes 12c' and 12g' of the gaskets 12c and 12g are closed by the cell window plates 12d disposed outside of the holes 12c' and 12g' (on opposite sides to the passage 12b in the flow cell 12). Portions of the holes 12c' and 12g' of the gaskets 12c and 12g are closed by the body 12a. Thus, a passage for a specimen and/or an eluant is formed so as to connect the internal passages 12k and 12m and the passage 12b.

The flow cell unit 12' also includes fasteners 12e disposed outside of the cell window plates 12d. The fasteners 12e are used for fixing the gaskets 12c and 12g and the cell window plates 12d. If the cell window plates 12d are fastened directly by the fasteners 12e, they may be broken depending upon how forces are applied to the fasteners 12e. Therefore, for example, O-rings 12f are provided so that forces are uniformly applied to the fasteners 12e. Each of the fasteners 12e has an opening portion 12e' located at the center of the fastener 12e. The opening portion 12e' extends through the fastener 12e. Light passes through the opening portion 12e'. In this manner, light is introduced into the passage 12b of the flow cell 12 through the opening portion 12e', and light that has passed through the flow cell is emitted through the opening portion 12e'. The flow cell used in the present invention is not limited to the above tapered one and may be a conventional straight flow cell having a cylindrical passage.

The chromatography data processing apparatus 20 performs various kinds of data analysis on the acquired chromatograms. For example, the chromatography data processing apparatus 20 has a hardware configuration including a controller (CPU), a memory, an external storage device, an input device such as a keyboard or a pointing device, and an output device such as a display device or a printer. Multi-channel time-series data outputted from the multi-channel detection device is stored in the memory.

The controller reads certain stored data (chromatograms) from the memory and displays them on the display device. Data stored in the memory may be read and displayed on the display device. Alternatively, data being transmitted from the multi-channel detection device 10 may be displayed in real time on the display device. Furthermore, the memory is also used as a working storage (buffer) when the controller performs operations. The external storage device may be a non-volatile memory. The external storage device stores therein chromatogram (data), the results of the data analysis and parameters (method) for various kinds of data analysis.

The controller applies a predetermined method (parameters) to the aforementioned chromatograms, performs certain data analysis, and has a function of displaying the results of data analysis on the display device or of printing out the results of data analysis from the printer. Furthermore, the chromatography data processing apparatus 20 (controller) also has a function of administering operations of the multi-channel detection device 10.

Calculation of Absorbance

The signal processing circuit 14 has a function of calculating an absorbance (AU) during measurement with a gradient elution method. In order to correct the baseline, the signal processing circuit 14 calculates an absorbance from the following formula:

$$AU = -\log_{10}(I/I_0)$$

where I is the intensity of light having a wavelength to be measured during measurement, and $I_0$ is the reference intensity of light.

Heretofore, the reference intensity of light having a wavelength to be measured at the beginning of measurement or the intensity of part of light having the same wavelength that had been isolated by a half mirror or the like has been used as the reference intensity of light $I_0$. According to the present invention, however, the reference intensity of light $I_0$ is calculated based upon the intensity of light having a wavelength different from the wavelength to be measured at the same point of time. Specifically, a wavelength that is not used for measurement of the sample is selected. For example, the intensities of light of 16 intervals about the selected wavelength (32 intervals in total) are averaged to obtain the reference intensity of light $I_0$. When the resolution of the wavelength is 1 nm, the reference intensity of light $I_0$ is an average of the intensity of light within a range of 32 nm. For example, the reference intensity of light $I_0$ is calculated by the following formula.

$$I_0 = \frac{\sum_{n=1}^{32} I_n}{32}$$

In practice, when a certain wavelength $\lambda_x$ is selected, the wavelength $\lambda_x$ is included in the 32 wavelengths. Therefore, the intensities of light of 32 wavelengths from the fifteenth shorter wavelength $\lambda_{(x-15)}$ than the selected wavelength $\lambda_x$ to the sixteenth longer wavelength $\lambda_{(x+16)}$ than the selected wavelength $\lambda_x$ are acquired and averaged. In the above formula, the intensity of light of the wavelength $\lambda_{(x-15)}$ is represented by $I_1$, and the intensity of light of the wavelength $\lambda_{(x+16)}$ is represented by $I_{32}$. In the present embodiment, the detector 13 is a multi-channel detector such as a photodiode array or a solid-state imaging device. Therefore, output signals of the detector 13 that correspond to those wavelengths can be known. Accordingly, the signal processing circuit 14 acquires each of values of $I_n$ from the corresponding output signal and calculates $I_0$.

A user may set the wavelength used to calculate the reference intensity of light $I_0$ (e.g., the above wavelength $\lambda_x$) depending upon the wavelength to be measured. For this setting, for example, a setting screen may be displayed on the display device of the chromatography data processing apparatus 20. Selection may be made by input signals from the input device. Then the chromatography data processing apparatus 20 may set the selection on the multi-channel detection device 10.

For example, variations of the baseline due to variations in index of refraction with a gradient elution method are found over the measured range of wavelengths. Furthermore, although the amount of variation of the baseline may be different depending upon the wavelength, the same tendency of variations is exhibited on each wavelength. Specifically, for example, if the baseline at the measured wavelength varies so as to increase in the plus direction, then the baselines at wavelengths other than the measured wavelength vary so as to increase in the plus direction at the same point of time and do not vary in the minus direction. Therefore, influence of variations of the baseline at the wavelength to be measured is reduced by correcting the baseline with the aforementioned reference intensity of light $I_0$ and calculating the absorbance.

Variation Examples

In the above embodiment, the reference intensity of light is calculated from an average of the intensities of light of 32 wavelengths about the wavelength that is different from the measured wavelength. Nevertheless, the present invention is not limited to this example. The number of wavelengths being averaged may be doubled. Thus, the intensities of light of 64 wavelengths may be averaged. Any different number of wavelengths being averaged may be used. Furthermore, the number of wavelengths used to calculate the reference intensity of light $I_0$ may be fixed or may be set by a user. If a user sets the number of wavelengths used to calculate the reference intensity of light $I_0$, the system may receive any input of numerical values or allow the user to select the number of wavelengths from among a plurality of preset values. It is preferable to perform this determination of the number of wavelengths along with the selection of the wavelength. Furthermore, only one wavelength may be used to calculate the reference intensity of light.

Furthermore, in the present embodiment, an average of the intensities of light with a plurality of wavelengths, rather than the intensity of light with one wavelength, is used to calculate the reference intensity of light $I_0$. Therefore, the noise can be reduced. Moreover, the reference intensity of light $I_0$ is measured at the same point of time. Therefore, for example, variations in intensity of light from the lamps, i.e., the light sources 11, which are caused by changes of the operation temperature, can advantageously be corrected as well.

In order to reduce the influence of the noise, it is preferable to increase the number of wavelengths used to calculate the reference intensity of light $I_0$. In the above embodiment, the number of samples is 32 or 64. The number of samples may be larger than those values. However, if the number of samples is increased excessively, the wavelength to be measured may be included in a range of wavelengths used to calculate the reference intensity of light $I_0$ depending upon the relationship between the wavelength $I_0$ selected for calculation of the reference intensity of light $I_0$ and the wavelength $\lambda_x$ to be measured. Thus, it is preferable to use a proper number of samples in order to avoid such a problem. For example, when the resolution of the wavelength is 1 nm as described above, the number of samples may be set to be about 100.

The wavelength to be measured is often in a relatively short wavelength region in a measurable range. In such a case, it is preferable to determine the reference intensity of light $I_0$ based upon the intensity of light in a wavelength region longer than the wavelength to be measured. Furthermore, if the wavelength to be measured needs to be in a longer wavelength region, then it is preferable to determine the reference intensity of light $I_0$ based upon the intensity of light in a wavelength region shorter than the wavelength to be measured.

In the above embodiment, the wavelength selected for calculating the reference intensity of light $I_0$ is used as the center wavelength, and the reference intensity of light $I_0$ is calculated based upon a predetermined number of wavelengths shorter and longer than the center wavelength. The present invention is not limited to such an example. For example, the shortest wavelength $\lambda_1$ may be specified, and the reference intensity of light $I_0$ may be calculated based upon a predetermined number of wavelengths (e.g., 32 wavelengths) longer than the shortest wavelength $\lambda_1$. Alternatively, the longest wavelength $\lambda_1$ may be specified, and the reference intensity of light $I_0$ may be calculated based upon a predetermined number of wavelengths (e.g., 32 wavelengths) shorter than the longest wavelength $\lambda_1$. Particularly, in a case where the reference intensity of light $I_0$ is calculated from a wavelength region longer than the wavelength to be measured, it is preferable to specify the shortest wavelength because the wavelength to be measured will not be included in wavelengths used to calculate the reference intensity of light $I_0$. Conversely, in a case where the reference intensity of light $I_0$ is calculated from a wavelength region shorter than the wavelength to be measured, it is preferable to specify the longest wavelength.

Furthermore, in the above embodiment, the correction of the baseline is performed by the signal processing circuit 14. The present invention is not limited to this example. The correction of the baseline may be performed by the chromatography data processing apparatus 20.

Experimental Results

The following experiments were conducted in order to prove the effects of the present invention. First, in order to confirm the effects of "reduction of variations of the baseline," a gradient elution method was carried out, and the degree of variations was compared between the conventional baseline and the baseline to which the present invention was applied.

Figure 4:
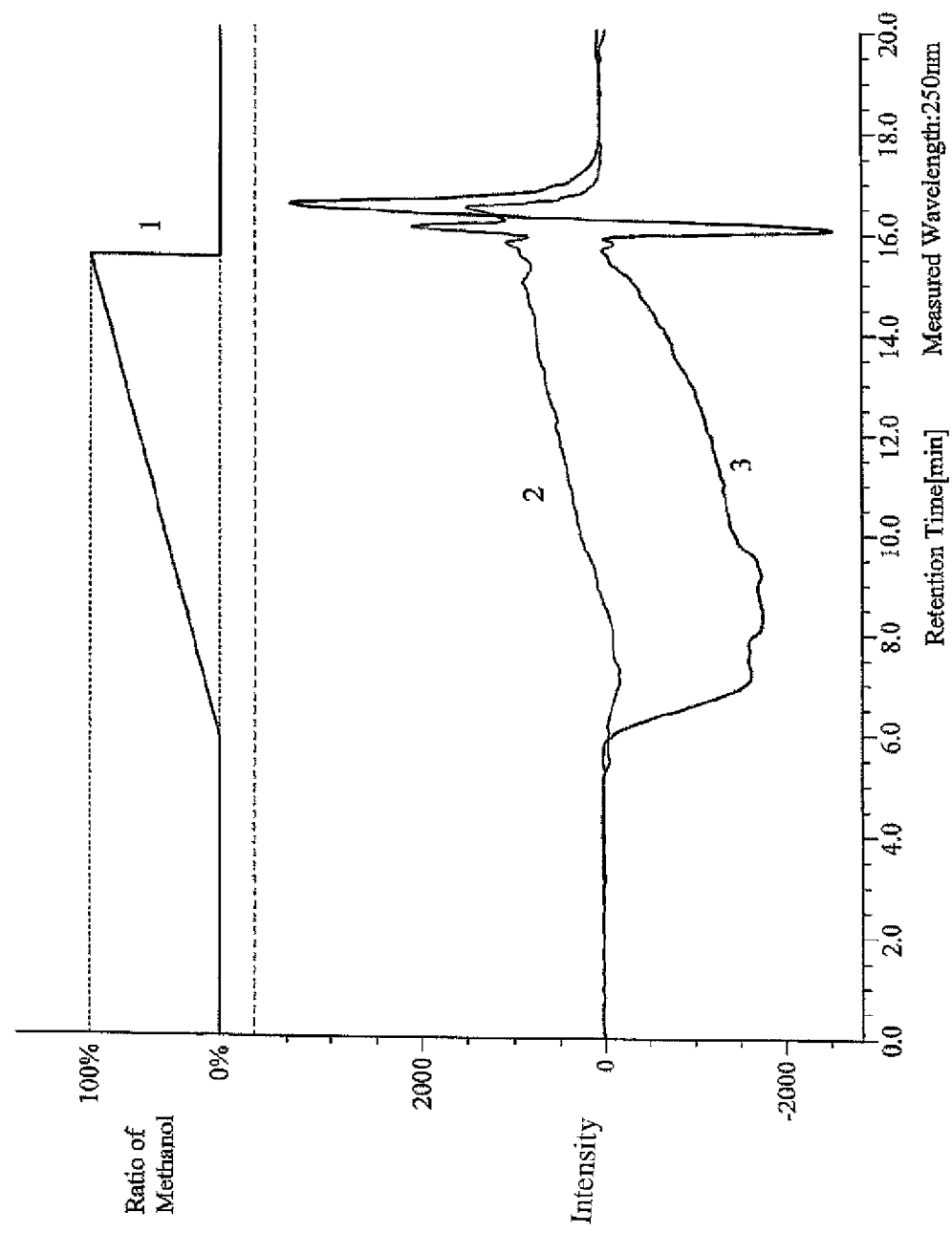
FIG. 4 is a graph showing experimental results.

FIG. 4 shows the results of comparison of the baseline variations with a gradient elution method using water and methanol, which are generally used in liquid chromatography, in a case where the measured wavelength was 250 nm. Line 1 shows changes of the composition ratio of methanol with time. Line 2 shows results of correcting the baseline in accordance with the present invention. Line 3 shows variations of the baseline in a case where no correction was performed. The reference intensity of light $I_0$ used to perform the correction was calculated with 32 wavelengths ranging from 400 nm to 431 nm. As is apparent from FIG. 4, the variation range of the baseline was 6,000 μAU in a case where no correction was performed. The correction improved the variation range of the baseline to 2,100 μAU.

Figure 5:
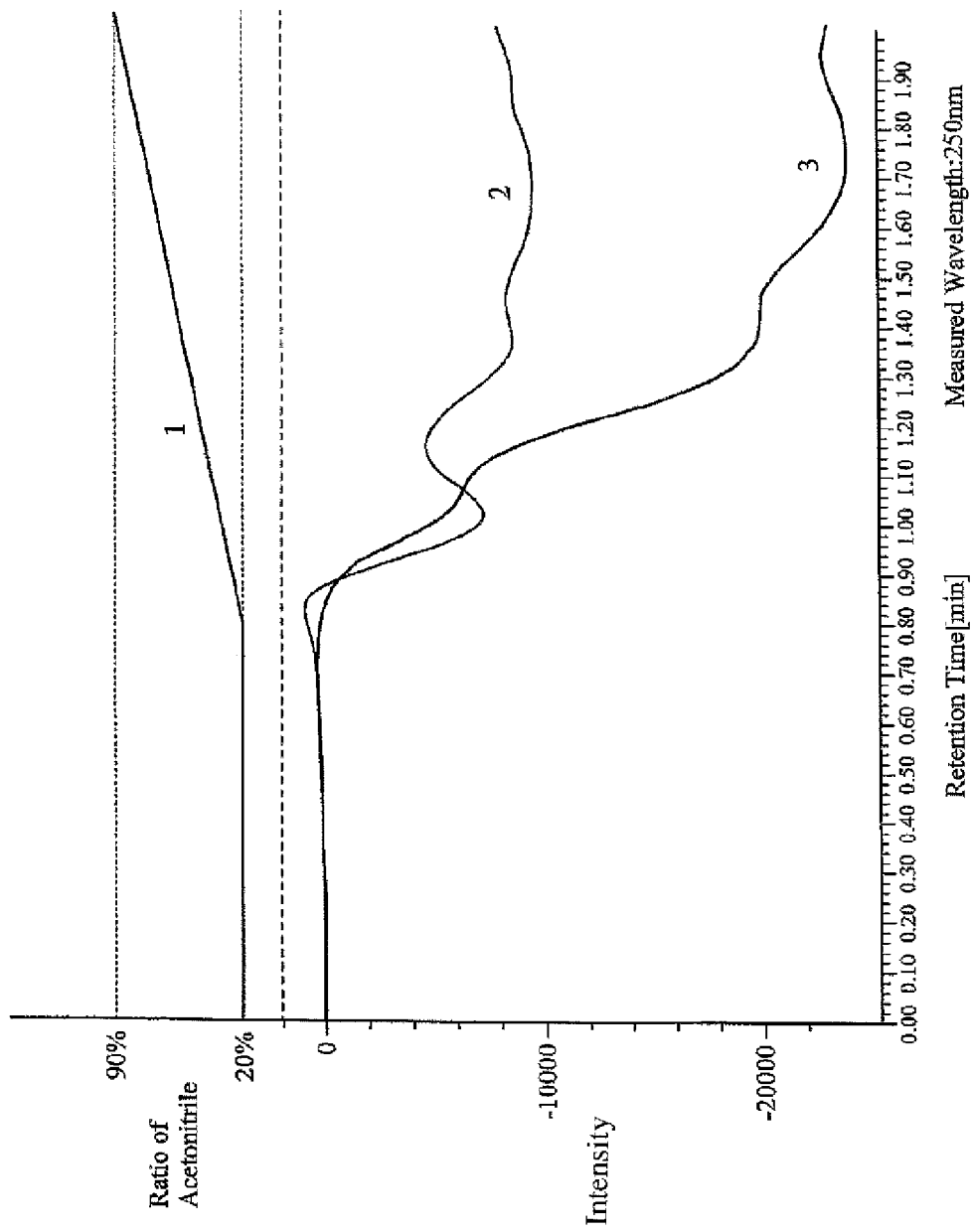
FIG. 5 is a graph showing experimental results.

FIG. 5 shows the results of comparison of the baseline variations with a gradient elution method using a solvent of water and acetonitrile in a case where the measured wavelength was 250 nm. Line 1 shows changes of the composition ratio of acetonitrile with time. Line 2 shows results of correcting the baseline in accordance with the present invention. Line 3 shows variations of the baseline in a case where no correction was performed. The reference intensity of light $I_0$ used to perform the correction was calculated with 32 wavelengths ranging from 400 nm to 431 nm. As is apparent from FIG. 5, the variation range of the baseline was 24,000 μAU in a case where no correction was performed. The correction improved the variation range of the baseline to 9,000 μAU.

Figure 6:
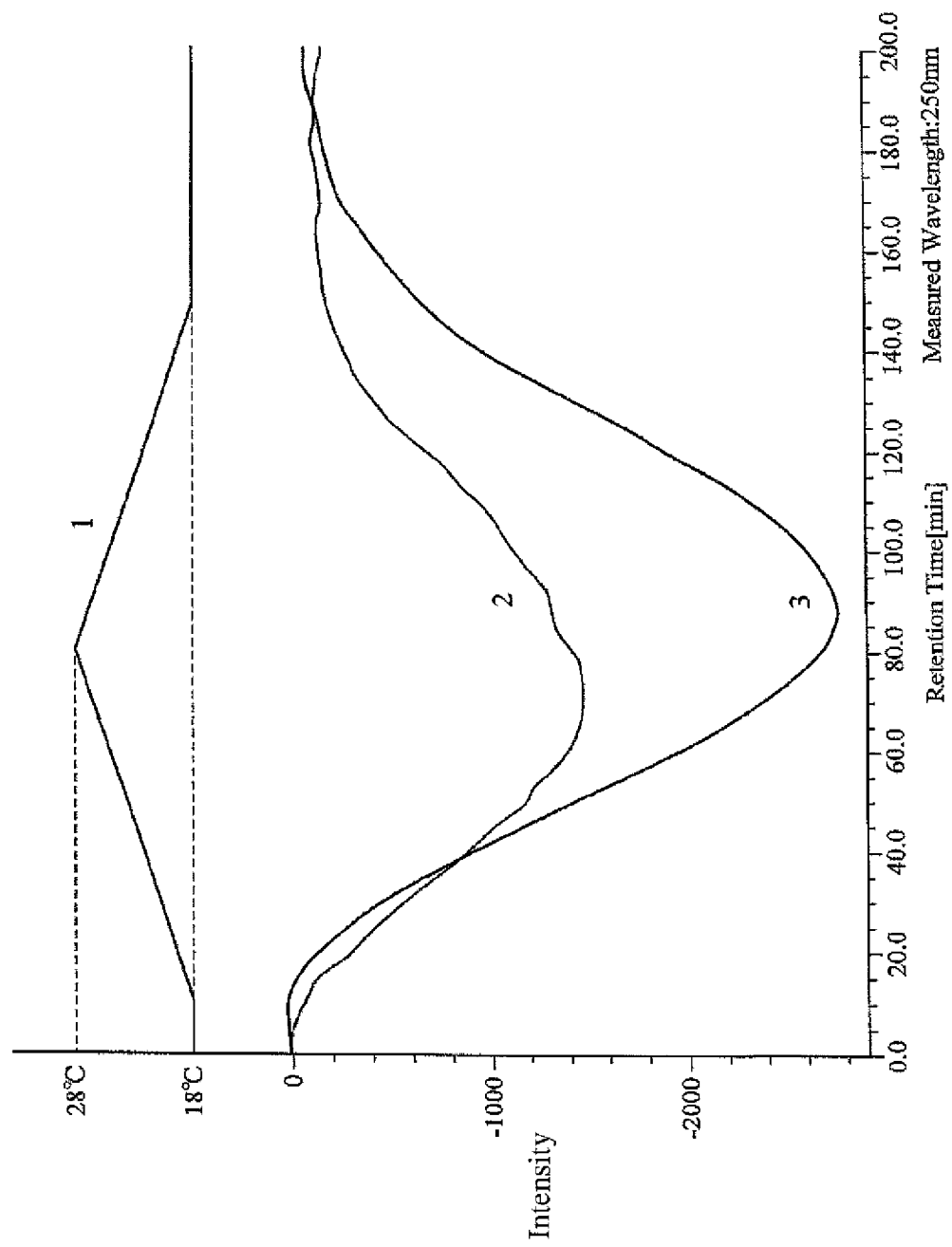
FIG. 6 is a graph showing experimental results.

Next, in order to confirm the effects of "improvement in stability of the baseline," the environmental temperature was varied, and the degree of drift was compared between the conventional baseline and the baseline to which the present invention was applied. FIG. 6 shows the results of comparison of the drifts with the measured wavelength of 250 nm in a case where the environmental temperature was changed from 18° C. to 28° C. and then returned to 18° C. while water was supplied. Line 1 shows changes of the air temperature outside the apparatus with time. Line 2 shows results of correcting the baseline in accordance with the present invention. Line 3 shows variations of the baseline in a case where no correction was performed. The reference intensity of light $I_0$ used to perform the correction was calculated with 32 wavelengths ranging from 400 nm to 431 nm. As is apparent from FIG. 6, the variation range of the baseline was 2,800 μAU in a case where no correction was performed. The correction improved the variation range of the baseline to 1,400 μAU.

Figure 7:
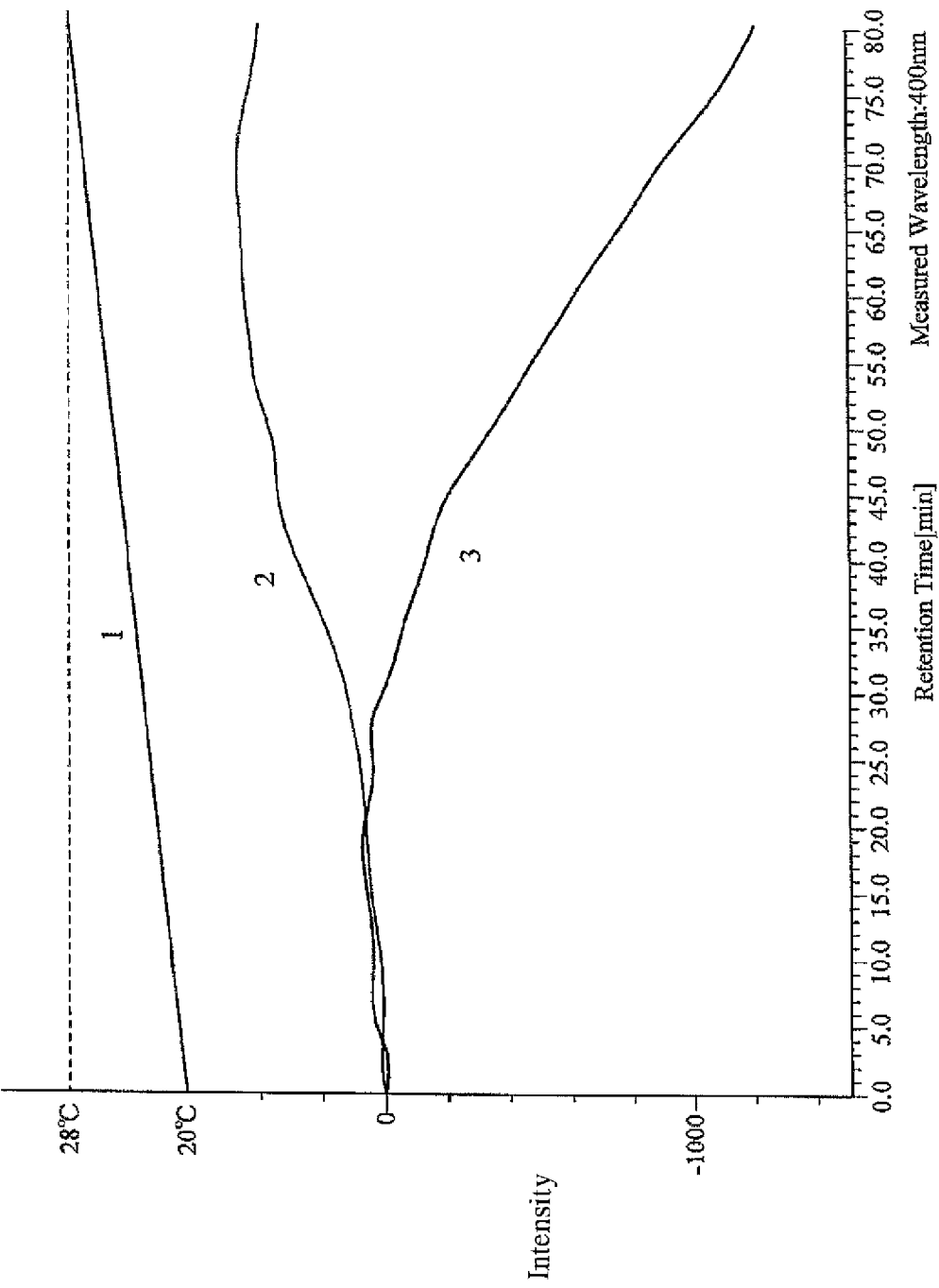
FIG. 7 is a graph showing experimental results.

FIG. 7 shows the results of comparison of the baseline drifts with the measured wavelength of 400 nm in a case where the environmental temperature was changed from 20° C. to 28° C. while water was supplied. Line 1 shows changes of the air temperature outside the apparatus with time. Line 2 shows results of correcting the baseline in accordance with the present invention. Line 3 shows variations of the baseline in a case where no correction was performed. The reference intensity of light $I_0$ used to perform the correction was calculated with 32 wavelengths ranging from 300 nm to 331 nm. As is apparent from FIG. 7, the variation range of the baseline was 1,300 μAU in a case where no correction was performed. The correction improved the variation range of the baseline to 500 μAU. In this example, the wavelengths used to calculate the reference intensity of light $I_0$ were shorter than the measured wavelength. Therefore, the positive and negative of the drifts were reversed.

Specifically, although the baseline varied in the same direction, the absolute values of the baseline tended to increase at shorter wavelengths. As a result, the positive and negative of the drifts were reversed as shown in FIG. 7. What is important is that the absolute value of the variation range of the corrected baseline becomes small. Thus, it has been confirmed that the present invention can be applied to either case where the wavelength used to calculate the reference intensity of light is longer or shorter than the wavelength to be measured.

Although certain preferred embodiments of the present invention have been shown and described in detail, it should be understood that various changes and modifications may be made therein without departing from the scope of the appended claims.

What is claimed is:

1. A chromatography system comprising:
   a flow cell to which a specimen is supplied;
   optics that directs light to the flow cell and outputs light that has passed through the flow cell, the optics having a function of wavelength dispersion of light;
   a multi-channel detector disposed at an output side of the optics, that receives respective wavelengths of the light dispersed by the optics; and
   a signal processing circuit provided in connection with the detector that obtains a chromatogram based on an intensity of light having a measuring wavelength to be measured that has been outputted from the detector, wherein
   the signal processing circuit corrects a baseline of the chromatogram based upon an average of intensities of light having a plurality of wavelengths that are detected simultaneously with the measuring wavelength and are longer than the measuring wavelength, wherein
   when correcting the baseline, the signal processing circuit calculates an absorbance by absorbance=−log 10($I/I0$)

where I is an intensity of light having a wavelength to be measured, and I0 is a reference intensity of light,
   the reference intensity of light is set based upon an average of intensities of light having a plurality of different wavelengths.

2. The chromatography system as recited in claim 1, wherein the plurality of wavelengths is at least 32 successive wavelengths.

3. A chromatography system comprising:
   a multi-channel detector having:
      a flow cell to which a specimen is supplied,
      optics that directs light to the flow cell and outputs light that has passed through the flow cell, the optics having a function of wavelength dispersion of light, and
      a detector disposed at an output side of the optics, that receives respective wavelengths of the light dispersed by the optics; and a controller that corrects a baseline of a chromatogram outputted from the multi-channel detector based upon an average of intensities of light having a plurality of wavelengths that are detected simultaneously with a measuring wavelength to be measured and are different from the measuring wavelength, wherein when correcting the baseline, the controller calculates an absorbance by $$absorbance = -\log 10(I/I0)$$

where I is an intensity of light having a wavelength to be measured, and I0 is a reference intensity of light, the reference intensity of light is set based upon an average of intensities of light having a plurality of different wavelengths.

4. The chromatography system as recited in claim 3, wherein the plurality of wavelengths is at least 32 successive wavelengths.

5. A signal processing apparatus in a chromatography system having a flow cell to which a specimen is supplied, optics that directs light to the flow cell and outputs light that has passed through the flow cell, the optics having a function of wavelength dispersion of light, and a detector disposed at an output side of the optics, the detector being a multi-channel detector that receives respective wavelengths of the light dispersed by the optics, the signal processing apparatus comprising:

an input part that is connected to the detector; and a signal processing circuit that obtains a chromatogram based on an intensity of light having a measuring wavelength to be measured that has been outputted from the detector, wherein the signal processing circuit corrects a baseline of the chromatogram based upon an average of intensities of light having a plurality of wavelengths that are detected simultaneously with the measuring wavelength and are longer than the measuring wavelength, wherein when correcting the baseline, the signal processing circuit calculates an absorbance by $$absorbance = -\log 10(I/I0)$$

where I is an intensity of light having a wavelength to be measured, and I0 is a reference intensity of light, the reference intensity of light is set based upon an average of intensities of light having a plurality of different wavelengths.

6. A non-transitory computer readable medium storing a program causing a computer to execute correction process for a chromatogram calculated based on an intensity of light having a measuring wavelength to be measured, the correction process comprising:

directing light to a flow cell to which a specimen is supplied;

outputting the light that has passed through the flow cell by optics having a function of wavelength dispersion of light;

receiving respective wavelengths of the light dispersed by the optics;

obtaining a chromatogram based on an intensity of light having the measuring wavelength; and correcting a baseline of the chromatogram based upon an average of intensities of light having a plurality of wavelengths that are detected simultaneously with the measuring wavelength and are different from the measuring wavelength, wherein the correcting further comprises calculating an absorbance by $$absorbance = -\log 10(I/I0)$$

where I is an intensity of light having a wavelength to be measured, and I0 is a reference intensity of light, the reference intensity of light is set based upon an average of intensities of light having a plurality of different wavelengths.

\* \* \* \* \*